United States Patent
Biro et al.

(10) Patent No.: US 6,751,823 B2
(45) Date of Patent: *Jun. 22, 2004

(54) MOTORIZED TOOTHBRUSH BRUSH TIP WITH TWO COUNTER-ROTATING BRUSH HEADS ROTATING ON A COMMON AXIS

(76) Inventors: Ladislau Biro, 14 Michael Dr., Metuchen, NJ (US) 08840; Howard Cohen, 201 E. 69th St., Apt. 314, New York, NY (US) 10021

( * ) Notice: Subject to any disclaimer, the term of this patent is extended or adjusted under 35 U.S.C. 154(b) by 0 days.

This patent is subject to a terminal disclaimer.

(21) Appl. No.: 10/084,519

(22) Filed: Feb. 25, 2002

(65) Prior Publication Data

US 2002/0157198 A1 Oct. 31, 2002

Related U.S. Application Data

(63) Continuation of application No. 09/338,750, filed on Jun. 23, 1999, now Pat. No. 6,349,442.

(51) Int. Cl.[7] .......................... A46B 13/02; A61C 17/34
(52) U.S. Cl. ............................................. 15/22.1; 15/28
(58) Field of Search .......................... 15/22.1, 28, 97.1, 15/21.1

(56) References Cited

U.S. PATENT DOCUMENTS

| 2,967,314 | A | * | 1/1961 | Kowalewski |
| 5,416,942 | A | * | 5/1995 | Baldacci |
| 5,625,916 | A | * | 5/1997 | McDougall |

* cited by examiner

*Primary Examiner*—Randall Chin
(74) *Attorney, Agent, or Firm*—Howard C. Miskin, Esq.; Gloria Tsui-Yip, Esq.

(57) ABSTRACT

A brush tip for a motorized toothbrush has a first brush head and a second brush head. The second brush head encircles the first brush head. A shaft has two cranks, each engaging one of the brush heads. Continuous same-direction rotation of the shaft causes the brush heads to counter-rotate about a common axis. Distal ends of the first set of bristles on the first brush head form a circular pattern and the distal ends of the second set of bristles on the second brush head form an elliptical pattern.

34 Claims, 8 Drawing Sheets

MOTORIZED TOOTHBRUSH BRUSH TIP WITH TWO COUNTER-ROTATING BRUSH HEADS ROTATING ON A COMMON AXIS

CROSS-REFERENCE TO RELATED APPLICATION

This application is a continuation in part of application Ser. No. 09/338,750, filed Jun. 23, 1999, issued on Feb. 26, 2002 as U.S. Pat. No. 6,349,442.

BACKGROUND OF THE INVENTION

The invention relates to toothbrushes, and more particularly relates to powered toothbrushes. In its most immediate sense, the invention relates to a brush tip for a powered toothbrush having two counter-rotating heads that rotate on a common axis.

In a conventional motorized toothbrush of the multi-head type, a disposable brush tip is detachably secured to the handle of the toothbrush. The tip has a plurality of brush heads, which oscillate (as by rotation) under the power of the motor. Each brush head has a plurality of tufts of bristles.

Existing motorized toothbrushes have relatively small "coverage", i.e. they do not clean large surface areas at one time. This is because the brush heads are relatively small. If they are made too large, they will put an excessive load on the motor.

Furthermore, some users operate such toothbrushes improperly. Instead of applying only light pressure, they force the bristles hard against the teeth. Under such conditions, the distal end of each tuft of bristles stays in the same place and the tufts twist themselves tightly in alternate directions. This makes the brushing less effective, because the bristles do not scrub the surfaces of the teeth.

It would be advantageous to provide a multi-head motorized toothbrush that would have greater coverage than conventional toothbrushes.

It would also be advantageous to provide a multi-head motorized toothbrush that would perform better even when the user applies excessive pressure against the tooth surfaces to be cleaned.

In accordance with the invention, a brush tip for a motorized toothbrush has a first brush head and a second brush head. The second brush head encircles the first brush head, and means are provided for differently accelerating the first and second brush heads in response to motion produced by the toothbrush motor.

Because the second brush head encircles the first brush head, the two head together have a relatively large area and, therefore, greater coverage. And, because the two brush heads are accelerated differently, their bristles do not twist themselves together even when pressed hard against the teeth.

In preferred embodiments, the first and second brush heads are accelerated in opposite directions, the first brush head is circular, and the second brush head is elliptical. The elliptical brush head provides greater coverage than a circular brush head and the opposite motions of the heads make it impossible for the bristles attached to the first brush head to twist into the bristles attached to the second brush head.

For toothbrushes of the type wherein the motor produces oscillating rotational motion of a shaft, a gear is mounted at the end of the shaft and is used to rotate the brush heads. For toothbrushes of the type wherein the motor produces reciprocating linear motion of an actuator, two connecting rods are used to convert this linear motion into oscillating rotational motion of the brush heads.

Such a brush tip is disclosed in commonly-owned pending patent application Ser. No. 09/338,750, filed Jun. 23, 1999, issued on Feb. 26, 2002 as U.S. Pat. No. 6,349,442, the entire disclosure of which (including the drawings) is hereby incorporated herein by reference. That pending patent application discloses two different head rotation mechanisms, each designed for use with a particular type of motorized toothbrush. One mechanism is designed for use with a motorized toothbrush wherein an actuator, such as a plunger, is linearly reciprocated. The other mechanism is designed for use with a motorized toothbrush wherein a shaft is rotationally oscillated.

Motorized toothbrushes generally use a battery-powered DC motor as a source of mechanical energy. This mechanical energy takes the form of a one-way rotation of a shaft that is mechanically coupled to the rotor of the DC motor. Therefore, for the above-discussed mechanisms to be usable, the motorized toothbrush must include a motion conversion mechanism that converts the one-way shaft rotation produced by the DC motor into linear reciprocation or into rotational oscillation. This increases cost of manufacture, diminishes power available to the toothbrush heads, and increases noise of the toothbrush during use. It would be advantageous to provide a brush tip for a motorized toothbrush wherein one-way rotation of a shaft can be used as the mechanical input to drive two counter-rotating heads that rotate about a common axis.

Furthermore, the mechanisms disclosed in the above-referenced allowed patent application require adjustment during assembly. Such adjustment has associated costs. It would be advantageous to provide a brush tip of this type that could be assembled with less adjustment, and therefore at reduced cost.

SUMMARY OF THE INVENTION

In accordance with the invention, first and second brush heads are provided. The first brush head is mounted for rotation about a brush head axis and has a first slot extending generally normal to the brush head axis. The second brush head encircles the first brush head, and is mounted for rotation about the brush head axis. The second brush head has a second slot extending generally normal to the brush head, and the first and second slots are on the same side of the brush head axis. And, an elongated shaft is provided. The shaft is mounted for rotation about a shaft axis, has a proximal end and a distal end, and forms first and second cranks. The first crank is located at the distal end of the shaft and engages the first slot, the second crank is located intermediate the first crank and the proximal end of the shaft and engages the second slot, and the cranks are offset with respect to each other.

This brush tip is suited for direct connection to a DC motor in the motorized toothbrush; the shaft can be coupled to the shaft of the motor without the need for an intermediate mechanism to change the rotation of the motor to linear reciprocation or rotational oscillation. And, assembly requires little adjustment because it is only necessary to drop the brush heads over the shaft so that the first slot and second slot engage the first and second cranks respectively. Alternatively, the brush tip can be assembled by simply pushing the distal end of the shaft through the second slot of the second brush head and into the first slot of the first brush head; in this instance, both the brush heads rotate until the second crank engages the second slot.

Advantageously, the shaft is a serpentine metal element, the first and second cranks extend away from the shaft axis in opposite directions, and the cranks occupy a common plane that contains the shaft axis. Such a shaft can be easily and inexpensively manufactured (as by stamping or bending).

In a particularly advantageous embodiment, the second brush head has an interior recess adjacent the second slot and a washer is mounted on the shaft between the first and second cranks so that it is located in the recess. As the shaft rotates, the washer keeps the first and second brush heads spaced apart, thereby preventing them from "chattering," i.e. from striking against each other as they rotate). This reduces noise during operation.

In accordance with the invention, the first brush head has a first set of bristles secured thereon forming a circular pattern and the second brush head has a second set of bristles secured thereon forming an elliptical pattern. The elliptical pattern on the second brush head provides a greater coverage than a conventional circular pattern and the opposite rotating motions of the first and second brush heads prevent the bristles from the first and second brush heads from twisting into each other.

BRIEF DESCRIPTION OF THE DRAWINGS

The invention will be better understood with reference to the following illustrative and non-limiting drawings, in which.

DETAILED DESCRIPTION OF PREFERRED EMBODIMENTS

In the following description, the same element is always indicated by the same reference numeral in all the Figures, and corresponding elements are indicated by primed reference numerals.

Figure 1:
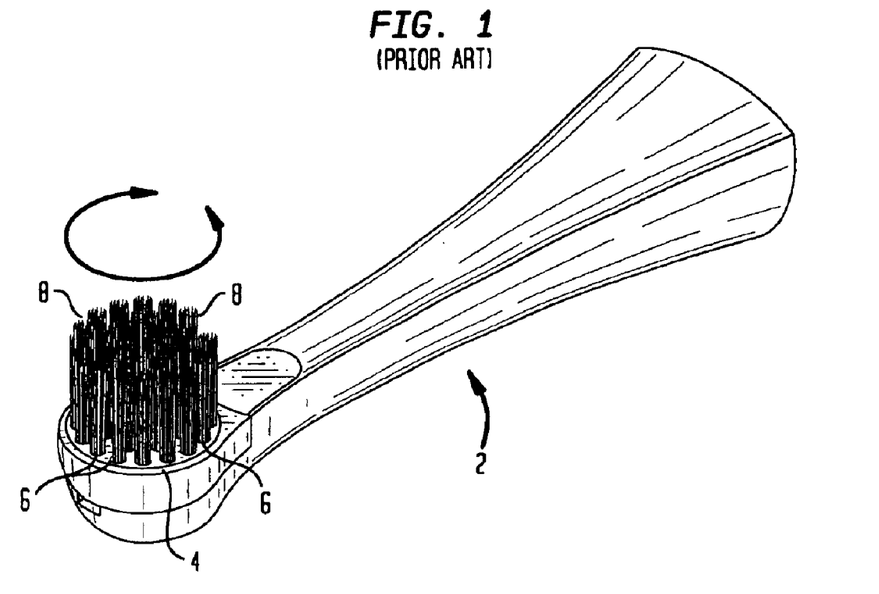
FIG. 1 illustrates a conventional motorized toothbrush with a brush tip of the single head type.

Turning first to FIG. 1, a conventional motorized brush tip generally indicated by reference numeral 2 has a brush head 4 on which tufts 6 of bristles 8 are secured. The brush head 4 is oscillated back and forth by a motor (not shown) while the user (not shown) brushes his or her teeth (not shown).

Figure 2:
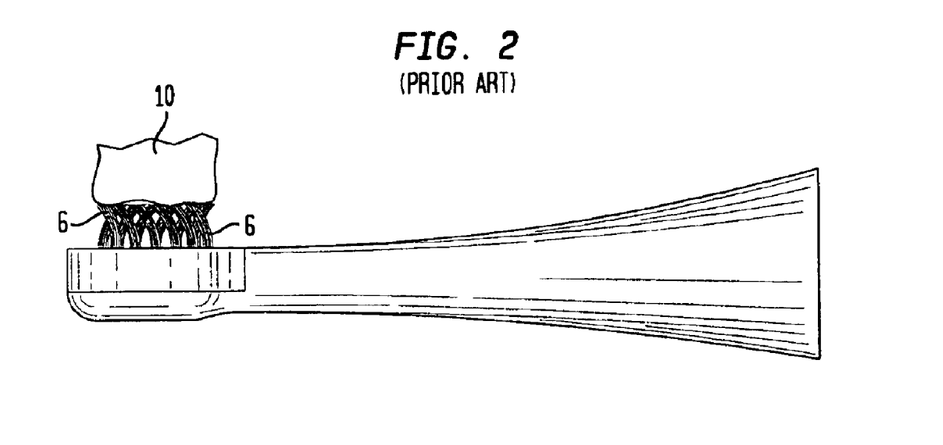
FIG. 2 illustrates how the bristles of the FIG. 1 toothbrush twist together when pressed against a tooth with excessive force.

To use the toothbrush properly, the distal ends of the bristles 8 should not press hard against the surfaces of the teeth. Under such conditions, the bristles 8 scrub the tooth surfaces and remove food particles etc. therefrom. However, as can be seen in FIG. 2, some users apply an excessive pressure to the toothbrush, causing the bristles 8 to press hard against the tooth surface 10. Under such conditions, the bristles 8 do not scrub the tooth surface 10. Instead, the distal ends of the bristles 8 stay fixed in position and the tufts 6 twist tightly against each other. This diminishes the cleaning effectiveness of the toothbrush and also excessively wears the brush tip 2.

Figure 3:
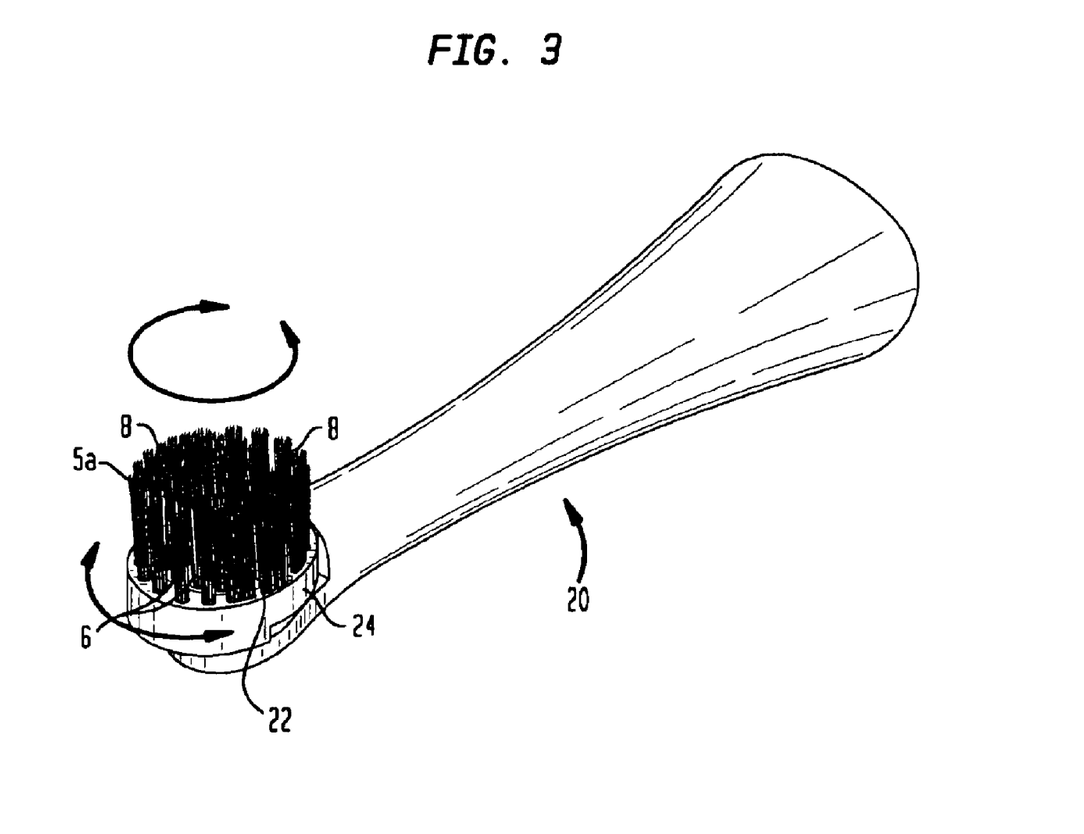
FIG. 3 illustrates a preferred embodiment of the invention.

In accordance with the preferred embodiment of the invention, a brush tip generally indicated by reference numeral 20 has a first brush head 22 and a second brush head 24. The second brush head 24 encircles the first brush head 22. The first brush head 22 is circular, and the second brush head 24 is elliptical. (Although the second brush head 24 is advantageously elliptical, this is not required and another non-circular shape can be used instead. Furthermore, the second brush head 24 is advantageously continuous, but need not be so. It may be made up of a plurality of segments, and may therefore have one or more gaps.). In further accordance with the preferred embodiment of the invention, means are provided to accelerate the brush heads 22 and 24 differently, i.e. to move in opposite directions. The preferred embodiment therefore provides coverage that is greater than the coverage provided by the brush heads, since the elliptical second brush head 24 swipes over a wider area than the surface areas of the brush heads. Furthermore, because the first and second brush heads 22 and 24 are accelerated differently, their bristles do not twist together in a knot if the user applies excessive pressure to the toothbrush.

In accordance with the preferred embodiment, the tufts 5a and 6 of bristles 8 on the first and second brush heads 22 and 24 are differently shaped. The tufts 5a are larger and have generally rectangular footprints, while the tufts 6 are smaller and have generally circular footprints. Although the tufts 5a and 6 of bristles 8 are illustrated as being supported by the first and second brush heads 22 and 24 in particular patterns, this is merely exemplary and is not a part of the invention. Other patterns can be used instead. The choice of the patterns in which the tufts 5a and 6 of bristles 8 are arranged is within the capability of a person skilled in the art.

Mechanisms by which the preferred embodiment may advantageously be operated will now be described in connection with FIGS. 3–4. However, before describing these mechanisms, it is necessary to describe two types of motorized toothbrushes with which the invention is intended to be used.

In one type of motorized toothbrush, the motor causes an actuator (e.g. a plunger) to reciprocate linearly. When the invention is intended for use with this type of toothbrush, this linear reciprocation must be converted to oscillating rotations of the brush heads 22, 24. In another type of motorized toothbrush, the motor causes oscillating rotation of a shaft. When the invention is intended for use with this type of toothbrush, the rotation of the shaft must be transmitted to the brush heads 22, 24. The first type of mechanism will be described first in connection with FIGS. 4–5 and the second type of mechanism will be described next in connection with FIG. 6.

Figure 4A:
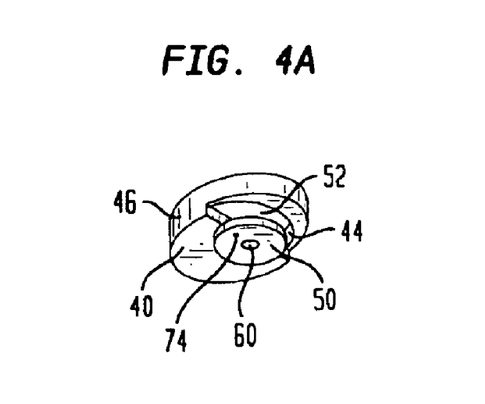
FIGS. 4A and 4B are, respectively, a view of a part and an exploded view of a first preferred structure for the FIG. 3 embodiment, this being suitable for use with a motorized toothbrush of the linear motor type.
Figure 4B:
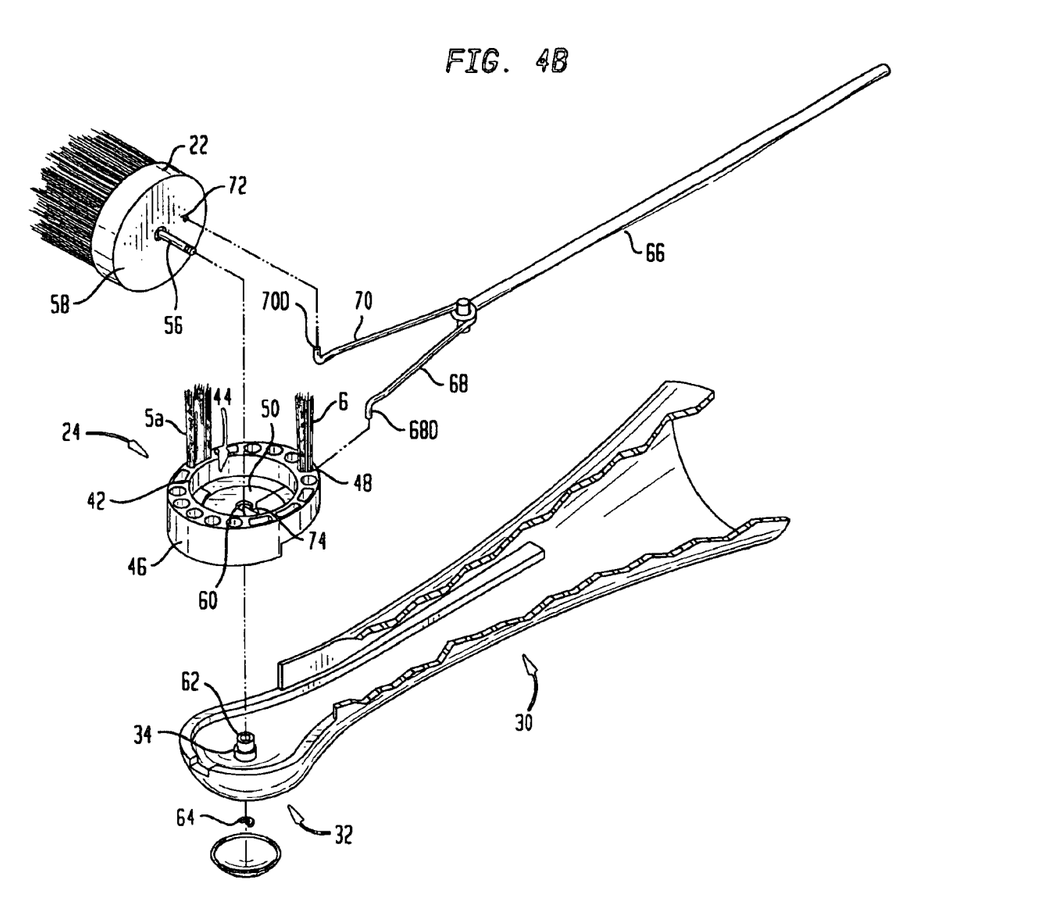

Referring now to FIG. 4, a housing 30 is adapted for attachment to the handle (not shown) of a motorized toothbrush. At the distal end 32 of the housing 30 is located a bearing post 34 upon which the second brush head 24 (described in more detail below) rotates when in use. The first brush head 22 is (as described in more detail below) located within the second brush head 24 in such a manner that the first brush head 22 is free to rotate.

The second brush head 24 has a bottom portion 40, from which a peripheral wall 42 extends upwardly. The interior surface of the wall 42 is cylindrical, creating a cylindrical well 44 in the center of the second brush head 24. (The exterior surface 46 of the wall 42 is elliptical, thereby creating an elliptical annulus 48 at the top of the wall 42 on which tufts 6 of bristles 8 can be supported.)

The surface 50 of the bottom portion 40 forms a bottom surface of the well 44, and a slot 52 is located in the wall 42. The slot 52 is parallel to the bottom surface 50 of the well 44.

The first brush head 22 is cylindrical. Tufts 6 of bristles 8 are supported on its top surface, and an axially extending axle pin 56 projects downwardly from its bottom surface 58. The axle pin 56 extends through a central hole 60 in the second brush head 24 and through a hole 62 in the center of the bearing post 34. A clip 64 at the distal end of the axle pin 56 holds the first brush head 22 within the second brush head 24, and attaches both of them to the housing 30 in such a manner that each brush head 22, 24 can rotate independently of the other. Advantageously but not necessarily, the brush heads 22, 24 are made of Delrin® or other suitable plastic, but this is not a part of the invention and other materials may be used instead.

As stated above, linear motion of a motor-driven actuator 66 must be converted to rotational motion of the first and second brush heads 22 and 24. To do this, first and second connecting rods 68 and 70 are used. The connecting rods 68 and 70 extend through the slot 52 and are formed of a single piece of wire that is generally V-shaped, with the vertex of the V being secured to the actuator 66. (In this preferred embodiment, the wire is bent into a circle at its vertex to facilitate connection with the actuator 66, but this is not required. Advantageously, the wire is of piano wire, or of e.g. nickel-titanium alloy, but other materials may be used instead.) The distal end 70D of the first connecting rod 70 is formed into a hook that engages with a recess 72 in the bottom surface 58 of the first brush head 22, and the distal end 68D of the second connecting rod 68 is formed into a hook that engages with a recess 74 in the bottom surface 50 of the well 44.

Figure 5A:
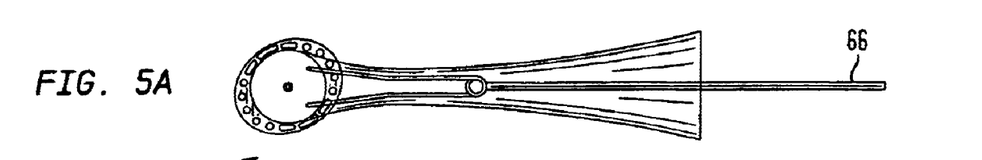
FIGS. 5A, 5B, and 5C illustrate the operation of the structure shown in FIG. 4.
Figure 5B:
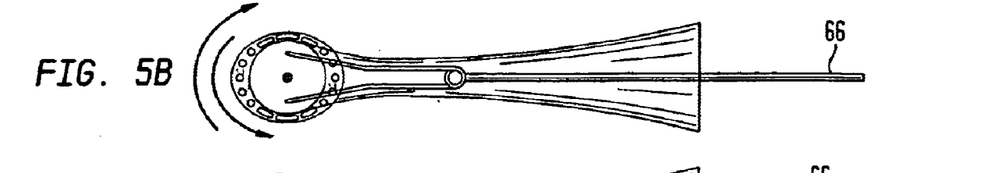
Figures 5C, 6:
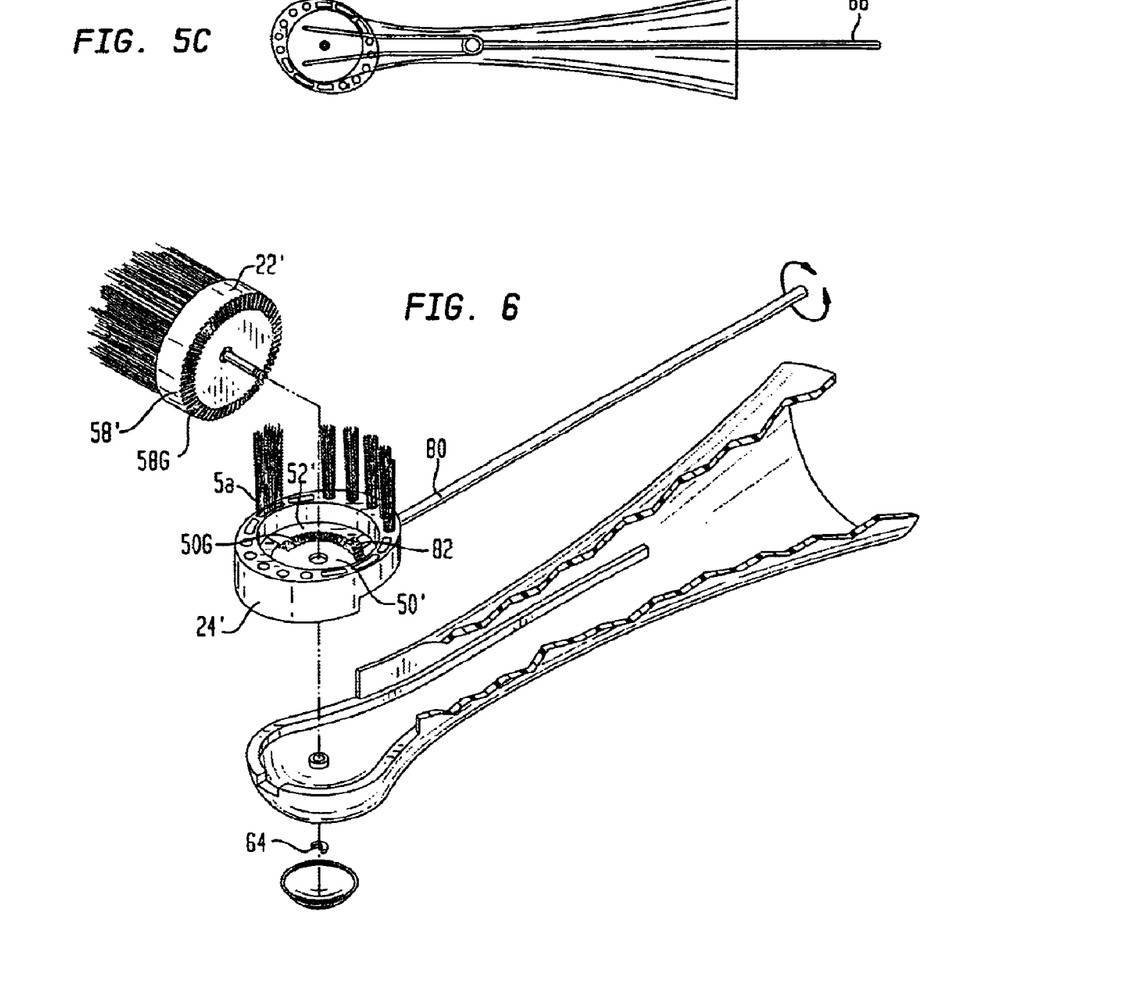
FIG. 6 illustrates the operation of a second preferred structure for the FIG. 3 embodiment, this being suitable for use with a motorized toothbrush of the oscillating motor type.

Turning now to FIGS. 5A–5C, when the actuator 66 is at its extreme rearward position (FIG. 5A), the first brush head 22 is rotated to its extreme clockwise position, the second brush head 24 is rotated to its extreme counterclockwise position, and the distal ends 68D and 70D are close together. As the actuator 66 is advanced (FIG. 5B), the connecting rods 68 and 70 move forwardly, their distal ends 68D and 70D move radially outwardly, the first brush head 22 moves counterclockwise, and the second brush head 24 moves clockwise. This continues until the actuator 66 is at its extreme forward position (FIG. 5C), when the first brush head 22 is at its most counterclockwise position, the second brush head 24 is at its most clockwise position, and the distal ends 68D and 70D are close together again. The actuator 66 then moves rearwardly, the above-described motions proceed in reverse, and the linear reciprocation of the actuator 66 is thereby converted to rotational oscillation of the brush heads 22, 24.

It will be understood from the above that the length of the slot 52 is selected to correspond to the arc through which the brushes 22, 24 are rotated during operation. In the preferred embodiment, this arc is 120°, but this is not part of the invention.

FIG. 6 shows an alternate structure, for use in instances wherein the motor (not shown) causes a shaft 80 to undergo rotational oscillation. In this structure, the first and second brush heads 22' and 24' have the same general shapes, but there are no connecting rods. Instead, toothed regions 50G and 58G are cut into the bottom surfaces 50' and 58', the shaft 80 extends through the slot 52', and a conical gear 82 at the distal end of the shaft 80 engages the toothed regions 50G and 58G.

It will be understood that the above description may not apply precisely to a production-engineered device. For example, although the surfaces 50, 58 are described as flat, they need not be precisely planar and may even be curved as long as the device as assembled works without excessive play or vibration. Likewise, although the connecting rods 68, 70 are advantageously straight, they may alternatively be slightly bent if this does not interfere with proper operation.

Figure 7:
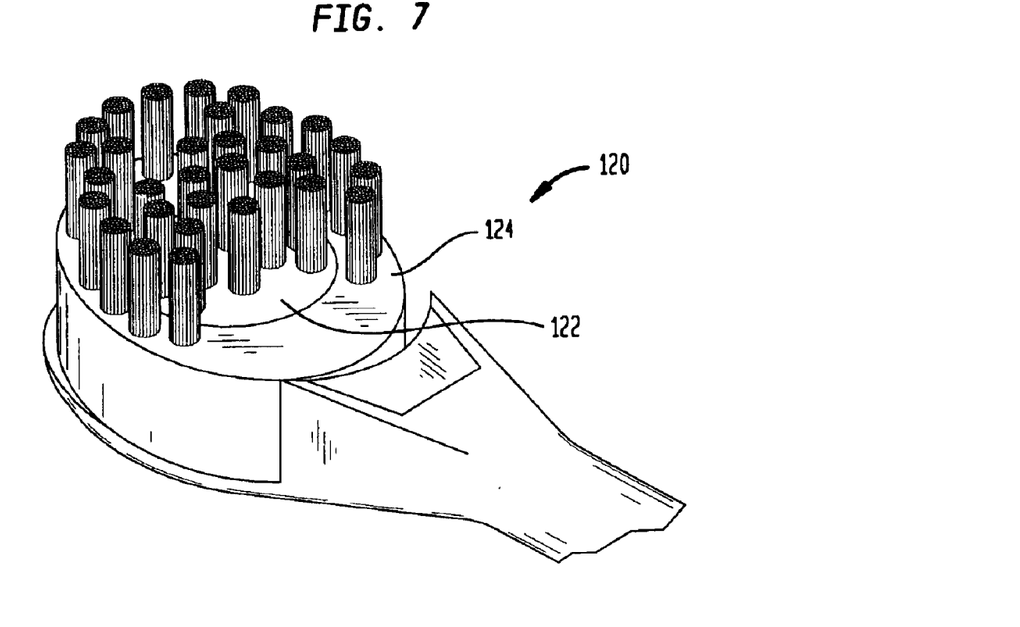
FIG. 7 shows the exterior of the brush end of a brush tip in accordance with a third preferred embodiment of the invention.
Figure 8:
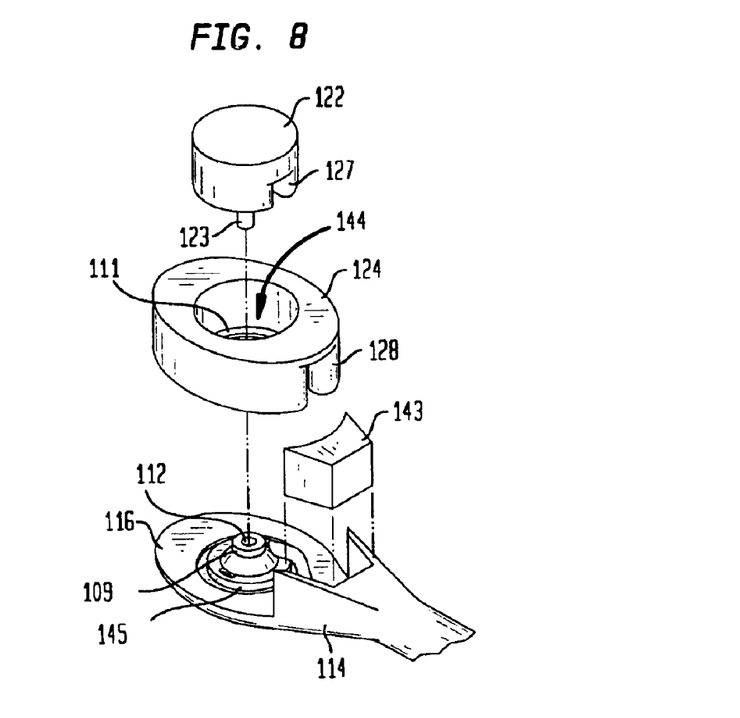
FIG. 8 is an exploded view of FIG. 7 from which the bristles have been omitted, illustrating how the brush heads of the third preferred embodiment are assembled.

Turning to FIGS. 7 and 8, a brush tip generally indicated by reference numeral 120 has a circular first brush head 122 encircled by a second brush head 124. In the preferred embodiment, both brush heads 122 and 124 are made of plastic and the second brush head 124 is non-circular (and is advantageously elliptical) but this is not a part of the invention.

The second brush head 124 has a central well 144 that is slightly larger than the first brush head 122. A lip 111 is located at the bottom of the well 144.

A metal axle 123 extends downwardly from the bottom of the first brush head 122, and passes through the open center at the bottom of the well 144. The axle 123 passes through a hole 112 in the central of a pedestal 109, which forms part of the plastic housing 114 of the brush tip and is secured in position by suitable means (such as a metal C-clip, not shown, located beneath the pedestal 109) in such a manner as to be free to rotate while being prevented from moving up and thereby becoming detached from the housing 114. In use, the first brush head 122 is located in the well 144, and the central pedestal 109 supports the bottom of the first brush head 122 to a position just above the lip 111. The second brush head 124 sits on the flat surface 116 of housing 114 with the lip 111 of the second brush head 124 located around the central circular region 145 of housing 114.

In this way, the first brush head 122 and the second brush head 124 are secured to the housing 114, with the second brush head 124 oscillating upon the flat surface 116 of the housing 114 and the first brush head 122 oscillating within the well 144 upon the pedestal 109. The second brush head 124 is constrained to oscillatorily rotate between the housing 114 and the first brush head 122 because the lip 111 prevents the second brush head 124 from sliding upwardly around the first brush head 122. Both the first and second brush heads 122 and 124 oscillatorily rotate about a common axis, which is the axis defined by the axle 123. And, as is explained in detail immediately below, the first and second brush heads 122 and 124 oscillatorily rotate in opposite directions.

The counter-oscillatory-rotation of the first and second brush heads 122 and 124 is accomplished by using an elongated serpentine metal shaft 125 that engages with the first and second brush heads 122 and 124 while rotating. The shaft 125 rotates about a shaft axis 126, and is advantageously secured to the rotor of a DC motor (not shown) in a motorized toothbrush (not shown). The shaft 125 is bent to form two cranks; a first crank 131 and a second crank 133. The first and second cranks 131 and 133 extend outwardly in opposite directions from the shaft axis 126, and the shaft 125 and first and second cranks 131 and 133 all advantageously lie in a single plane that includes the shaft axis 126. Although this is not required, it is advantageous because it permits the shaft 125 to be easily formed into the required shape, as by bending or stamping.

Figure 9:
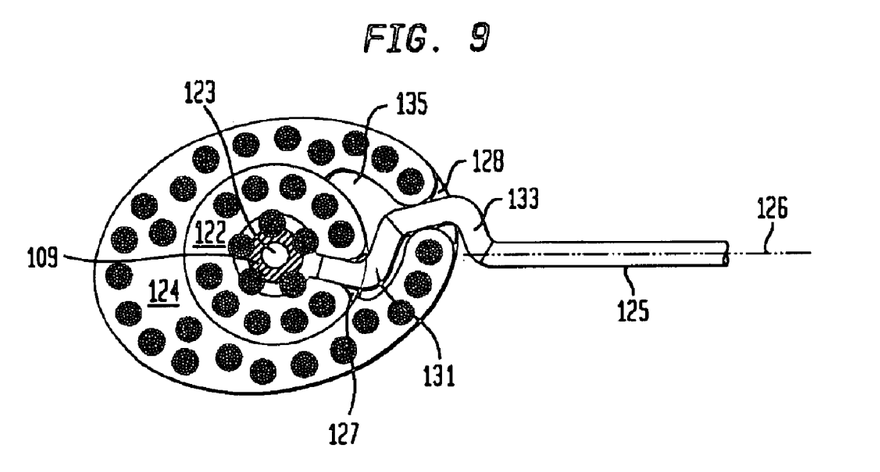
FIGS. 9, 10, and 11 schematically illustrate the principle of operation of a third preferred embodiment of the invention.
Figure 10:
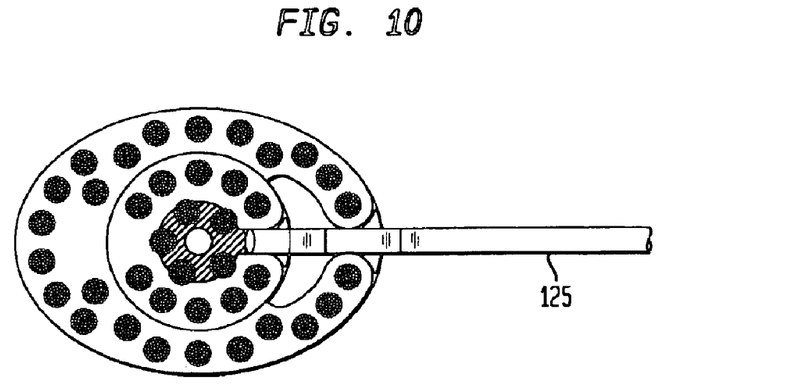
Figure 11:
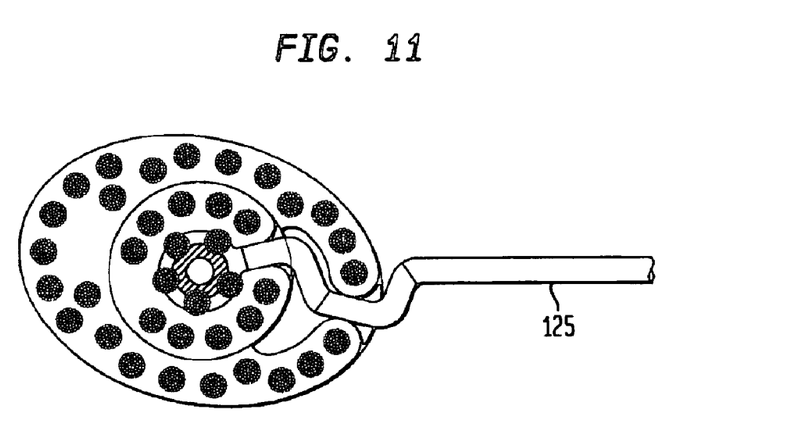

The first brush head 122 has a first slot 127, and the distal end of the first crank 131 engages the first slot 127. The second brush head 124 has a second slot 128, and the second crank 133 engages the second slot 128. As used herein, the term "slot" includes any opening that can receive the corresponding crank. For example, the first slot 127 can be a blind bore within the first brush head 122, and the second slot 128 can be any through-extending opening. In the preferred embodiments, the first and second slots 127 and 128 extend down to the bottoms of the first and second brush heads 122 and 124 to facilitate assembly. As can be seen in FIGS. 9, 10 and 11, as the shaft 125 is rotated around shaft axis 126, the first crank 131 not only rotates and moves up and down within the first slot 127, but also causes the first brush head 122 to oscillatorily rotate about the axis of the axle 123. The second crank 133 performs a similar function with respect to the second brush head 124; as the shaft 125 rotates, the second crank 133 not only rotates and moves up and down within the second slot 128, but also causes the second brush head 124 to oscillatorily rotate around the first brush head 122 and about the axis of the axle 123. Because the first crank 131 and the second crank 133 point in opposite directions away from the shaft axis 126, they cause the brush heads 122 and 124 to oscillatorily rotate in opposite directions, i.e. to counter-rotate. As a result, the first and second brush heads 122 and 124 counter-oscillatorily-rotate about a common axis, namely the axis of the axle 123.

In this preferred embodiment, the second brush head 124 has an interior recess 135 adjacent the second slot 128. The interior recess 135 provides clearance for that portion of the shaft 125 that connects the first crank 131 with the second crank 133. And, in this preferred embodiment, the first and second brush heads 122 and 124 may "chatter" during use, i.e. they strike each other because they vibrate side to side as they rotate. The chattering occurs because it would be too expensive to make all the parts with exactly matching tolerances and to support the brush heads 122 and 124 so that they do not move from side to side as they rotate.

Figure 12:
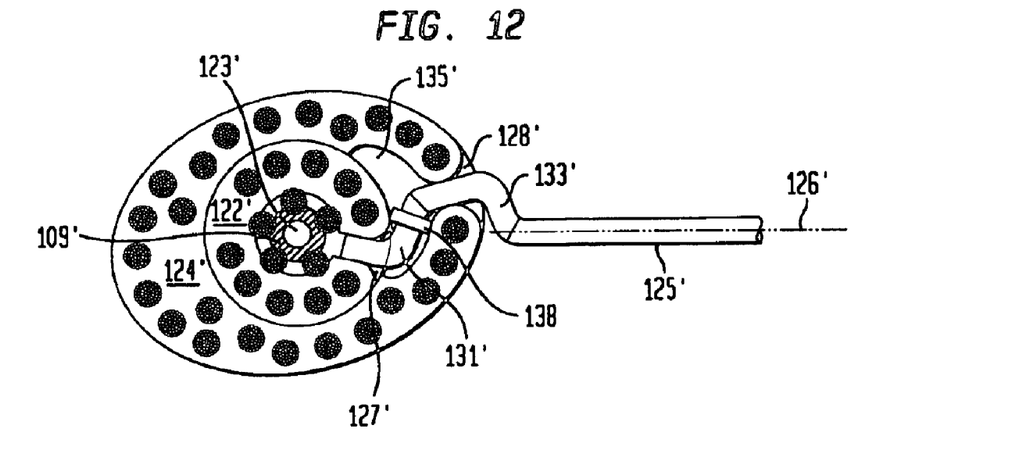
FIGS. 12, 13, and 14 schematically illustrate the principle of operation of a fourth preferred embodiment of the invention.
Figure 13:
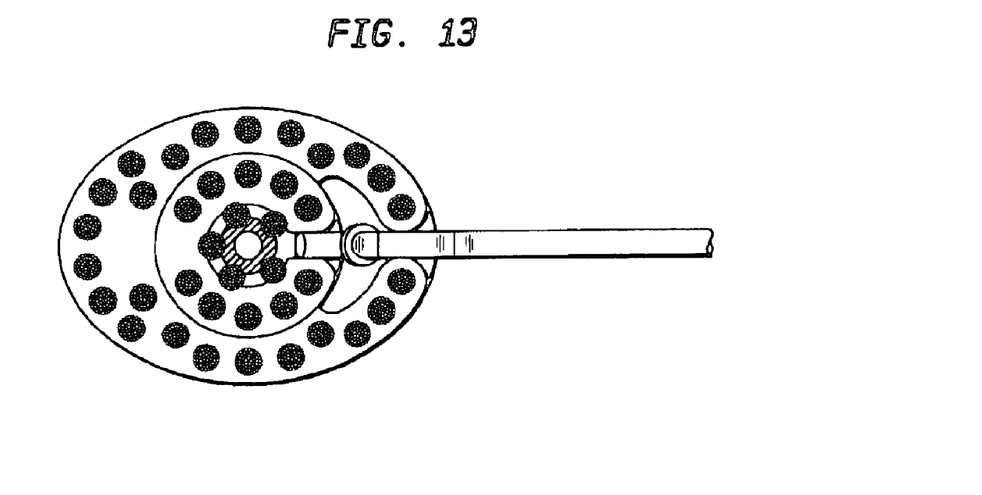
Figure 14:
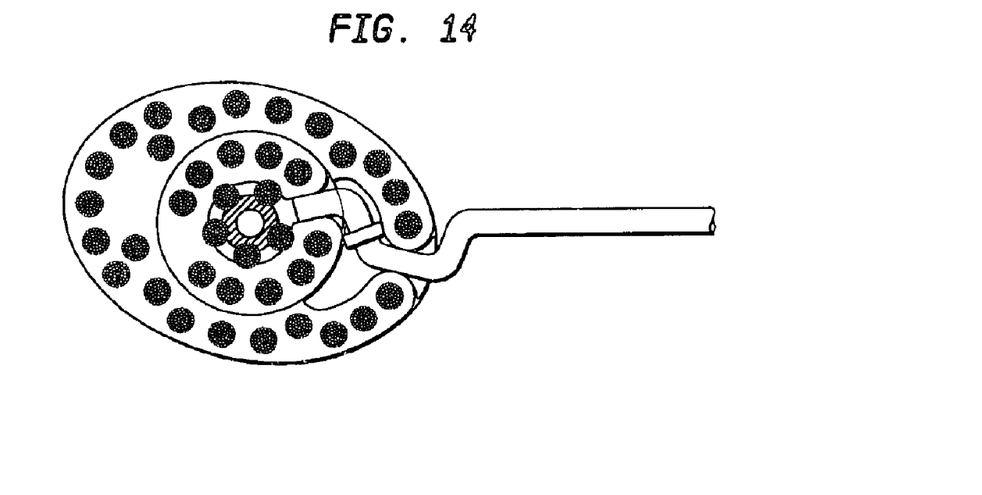

In the alternate preferred embodiment illustrated in FIGS. 12, 13 and 14, all parts are identical to the embodiment shown in FIGS. 9, 10 and 11, and are indicated by a primed numeral, e.g. shaft 125'. This alternate preferred embodiment has a collar 138 located on the shaft 125', between the first and second cranks 131' and 133', and the collar 138 rotates within the interior recess 135'. The collar 138 keeps the first and second brush heads 122' and 124' spaced apart and therefore prevents them from chattering.

To assemble the preferred embodiments shown in FIGS. 7–14, the shaft 125 or 125' is initially mounted within the housing 114 or 114' with the housing cap 143 or 143' uninstalled. Then, the second brush head 124 or 124' is put in place with the second slot 128 or 128' engaging the second crank 133 or 133'. This causes the shaft 125 or 125' to rotate to a position that allows the second brush head 124 or 124' to rest upon the surface 116 or 116' of the housing 114 or 114' with the lip 111 or 111' to just clear the central circular region 145 or 145' of the housing 114 or 114'. Next, the first brush head 122 or 122' is put in place and is positioned such that the first slot 127 or 127' engages the first crank 131 or 131'. The axle 123 or 123' is introduced in the hole 112 or 112' and the first brush head 122 or 122' is pressed down until the bottom of the brush head 122 or 122' rests upon the lip 111 or 111'. Finally, the axle 123 or 123' is locked in place (as by a C-clip, not shown) and the housing cap 143 or 143' is pressed in place.

Figure 15A:
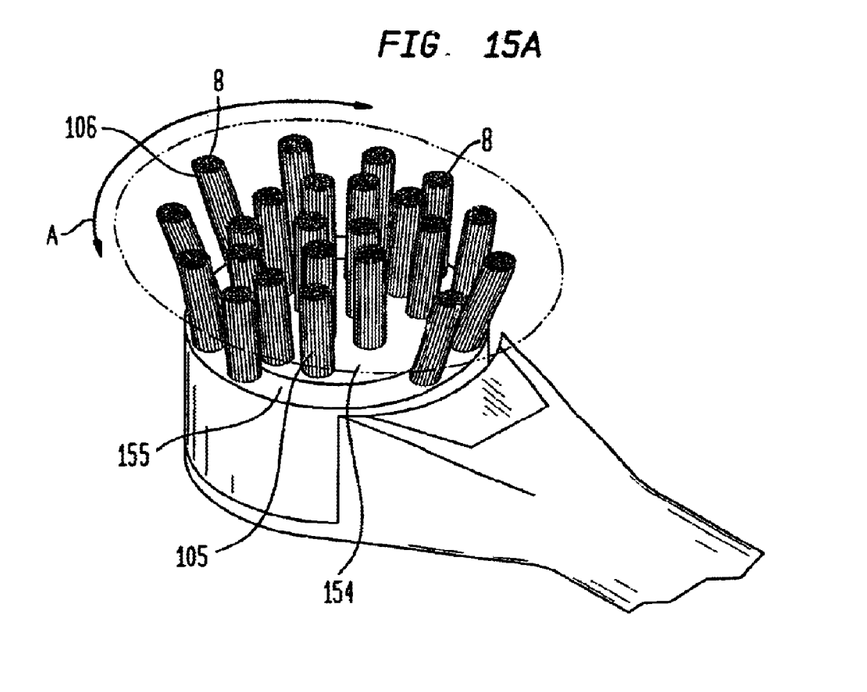
FIGS. 15A and 15B shows the exterior of the brush end of a brush tip in accordance with a fifth preferred embodiment of the invention.
Figure 15B:
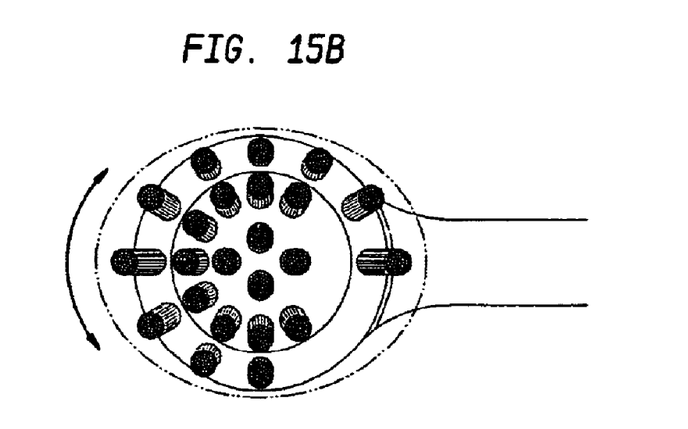

FIGS. 15A and 15B shows another preferred embodiment similar to those shown in FIGS. 7–14, having a circular first brush head 154 and a second brush head 155 encircling the first brush head 154. The assembly and drive mechanism of this embodiment may be any of the embodiments described above. Similar to the embodiments described above, each brush head 154 and 155 has a plurality of tufts 105 and 106 of bristles 8 mounted thereon respectively. Each tuft 105 and 106 of bristles 8 are shown to have similar sized circular footprints, although tufts 105 and 106 with different size and shape footprints may be used. As shown in FIGS. 15A and 15B, tufts 105 extend vertically from the first brush head 154 and tufts 106 extend from the second brush head 155 at an angle away from the first brush head 154. The distal ends of bristles 8 of tufts 105 on the first brush head 154 form a circular pattern and the distal ends of bristles 8 of tufts 106 on the second brush head 155 form an elliptical pattern (as illustrated by arrow A). Distal ends of bristles 8 of tufts 105 and 106 on the first and second brush heads 154 and 155, respectively, may form other patterns such as square, diamond, or other non-circular patterns. Similar to the brush head 24, the second brush head 155 may be continuous, but need not be so. It may be made up of a plurality of segments, and may therefore have one or more gaps.

Although at least one preferred embodiment of the invention has been described above, this description is not limiting and is only exemplary. The scope of the invention is defined only by the claims, which follow:

What we claim is:

1. A brush tip for a motorized toothbrush, comprising:
   a first brush head mounted for rotation about a brush head axis and having a first slot extending generally normal to said brush head axis;
   a second brush head mounted for rotation about said brush head axis and having an second slot extending generally normal to said brush head axis, said second brush head encircling the first brush head in such a manner that the first and second slots are on the same side of the brush head axis; and
   an elongated shaft mounted for rotation about a shaft axis, said shaft having a proximal end and a distal end and forming first and second cranks, said first crank being located at the distal end of the shaft and engaging said first slot, said second crank being located intermediate said first crank and said proximal end of said shaft and engaging said second slot, and said first and second cranks extending outwardly in opposite directions from said shaft axis.

2. The brush tip of claim 1, wherein said elongated shaft is a rod and said first and second cranks are bent regions of said rod.

3. The brush tip of claim 1, wherein said first and second cranks occupy a common plane that contains said shaft axis.

4. The brush tip of claim 1, wherein said shaft is a serpentine element.

5. The brush tip of claim 1, wherein said second brush head has an interior recess adjacent the second slot.

6. The brush tip of claim 5, further comprising a washer mounted upon said shaft between said first and second cranks and located within said recess.

7. The brush tip of claim 1 further comprising a first set of bristles extending from said first brush head, distal ends of said first set of bristles forming a circular pattern and a second set of bristles extending from second brush head, distal ends of said second set of bristles forming a non-circular pattern.

8. The brush tip of claim 7 wherein said distal ends of said second set of bristles forming an elliptical pattern.

9. The brush tip of claim 7 wherein said first and second sets of bristles extending substantially vertically from said first and second brush heads, respectively.

10. The brush tip of claim 7 wherein said first and second sets of bristles extending from said first and second brush heads, respectively, at an angle.

11. The brush tip of claim 7 wherein said first set of bristles extending substantially vertically from said first brush head and said second set of bristles extending from said second brush head at an angle away from said first brush head.

12. The brush tip of claim 1 wherein said second brush head being continuous.

13. The brush tip of claim 1 wherein said second brush head comprises a plurality of segments having gaps therebetween.

14. A brush tip for a motorized toothbrush, comprising:
a first brush head mounted for rotation about a brush head axis and having a first slot extending generally normal to said brush head axis;
a second brush head mounted for rotation about said brush head axis, having an second slot extending generally normal to said brush head axis, and having an interior recess adjacent said second slot, said second brush head encircling said first brush head in such a manner that said first and second slots are on the same side of the brush head axis; and
an elongated shaft mounted for rotation about a shaft axis, said shaft having a proximal end and a distal end and having first and second serpentine cranks, said first crank being located at the distal end of said shaft and engaging said first slot, said second crank being located intermediate said first crank and said proximal end of said shaft and engaging said second slot, and said first and second cranks extending outwardly in substantially opposite directions from said shaft axis and occupying a common plane that contains said shaft axis.

15. The brush tip of claim 14, further comprising a collar mounted on said shaft between said first and second cranks and located within said recess.

16. The brush tip of claim 15, wherein said first and second brush heads are made of plastic and said collar is made of elastomer.

17. The brush tip of claim 14 wherein said second brush head being continuous.

18. The brush tip of claim 14 wherein said second brush head comprises a plurality of segments having gaps therebetween.

19. A brush tip for a motorized toothbrush having a toothbrush motor, comprising:
a first set of bristles extending from a first brush head, distal ends of said first set of bristles forming a circular pattern;
a second set of bristles extending from a second brush head, distal ends of said second set of bristles forming a non-circular pattern, said second set of bristles encircling said first set of bristles; and
means for rotating said first and second sets of bristles in opposite senses about a common axis of rotation, said rotating means adapted to response to motion produced by the toothbrush motor.

20. The brush tip of claim 19 wherein said distal ends of said second sets of bristles forming an elliptical pattern.

21. The brush tip of claim 19 wherein said first and second sets of bristles extending substantially vertically from said first and second brush heads, respectively.

22. The brush tip of claim 19 wherein said first and second sets of bristles extending from said first and second brush heads, respectively, at an angle.

23. The brush tip of claim 19 wherein said first set of bristles extending substantially vertically from said first brush head and second set of bristles extending from said second brush head at an angle away from said first brush head.

24. A brush tip for a motorized toothbrush having a toothbrush motor, comprising:
a first set of bristles extending from a first brush head, distal ends of said first set of bristles forming a circular pattern;
a second set of bristles extending from a second brush head, distal ends of said second set of bristles forming a non-circular pattern, said second brush head encircling said first brush head; and
means for differently accelerating said first and second sets of bristles, said accelerating means adapted in response to motion produced by said toothbrush motor.

25. The brush tip of claim 24, wherein said distal ends of said second set of bristles forming an elliptical pattern.

26. The brush tip of claim 24, wherein said differently accelerating means causes said first and second sets of bristles to rotate in opposite senses about a common axis of rotation.

27. The brush tip of claim 26, wherein said motorized toothbrush has a shaft and produces rotational motion of said shaft, and wherein said differently accelerating means converts said rotational motion into oscillating rotational motion of said first and second sets of bristles.

28. The brush tip of claim 26, wherein said motorized toothbrush has an actuator and produces reciprocating linear motion of an actuator, and wherein said differently accelerating means converts said linear motion into oscillating rotational motion of said first and second sets of bristles.

29. The brush tip of claim 24 wherein said second brush head being continuous.

30. The brush tip of claim 24 wherein said second brush head comprises a plurality of segments having gaps therebetween.

31. A motorized toothbrush having a brush tip comprising:
a first brush head mounted for rotation about a brush head axis and having a first slot extending generally normal to said brush head axis;
a second brush head mounted for rotation about said brush head axis and having a second slot extending generally normal to said brush head axis, said second brush head encircling the first brush head in such a manner that the first and second slots are on the same side of the brush head axis; and
an elongated shaft mounted for rotation about a shaft axis, said shaft having a proximal end and a distal end and forming first and second cranks, said first crank being located at the distal end of the shaft and engaging said first slot, said second crank being located intermediate said first crank and said proximal end of said shaft and engaging said second slot, and said first and second cranks extending outwardly in opposite directions from said shaft axis.

32. A motorized toothbrush having a brush tip comprising:
a first brush head mounted for rotation about a brush head axis and having a first slot extending generally normal to said brush head axis;

a second brush head mounted for rotation about said brush head axis, having a second slot extending generally normal to said brush head axis, and having an interior recess adjacent said second slot, said second brush head encircling said first brush head in such a manner that said first and second slots are on the same side of the brush head axis; and an elongated shaft mounted for rotation about a shaft axis, said shaft having a proximal end and a distal end and having first and second serpentine cranks, said first crank being located at the distal end of said shaft and engaging said first slot, said second crank being located intermediate said first crank and said proximal end of said shaft and engaging said second slot, and said first and second cranks extending outwardly in substantially opposite directions from said shaft axis and occupying a common plane that contains said shaft axis.

33. A toothbrush having a toothbrush motor and a brush tip comprising:

a first set of bristles extending from a first brush head, distal ends of said first set of bristles forming a circular pattern;

a second set of bristles extending from a second brush head, distal ends of said second set of bristles forming non-circular pattern, said second set of bristles encircling said first set of bristles; and means for rotating said first and second sets of bristles in opposite senses about a common axis of rotation, said rotating means adapted to respond to motion produced by the toothbrush motor.

34. A toothbrush having a toothbrush motor and a brush tip comprising:

a first set of bristles extending from a first brush head, distal ends of said first set of bristles forming a circular pattern;

a second set of bristles extending from a second brush head, distal ends of said second set of bristles forming a non-circular pattern, said second brush head encircling said first brush head; and means for differently accelerating said first and second sets of bristles, said accelerating means adapted to respond to motion produced by the toothbrush motor.

* * * * *